United States Patent
Chang

[11] Patent Number: 6,117,982
[45] Date of Patent: *Sep. 12, 2000

[54] CONJUGATES OF MICROBEADS AND ANTIBODIES SPECIFIC FOR T LYMPHOCYTES AND THEIR USE AS IN VIVO IMMUNE MODULATORS

[75] Inventor: Tse Wen Chang, Houston, Tex.

[73] Assignee: Tanox, Inc., Houston, Tex.

[*] Notice: This patent is subject to a terminal disclaimer.

[21] Appl. No.: 08/046,364

[22] Filed: Apr. 8, 1993

Related U.S. Application Data

[63] Continuation of application No. 07/819,449, Jan. 10, 1992, abandoned, and a continuation-in-part of application No. 07/688,000, Apr. 19, 1991.

[51] Int. Cl.[7] .................................................. C07K 16/00
[52] U.S. Cl. .................. 530/391.1; 530/388.75; 530/389.6; 530/387.1; 424/178.1
[58] Field of Search ............................ 530/391.1, 388.75, 530/389.6, 387.1; 424/858, 450, 178.1

[56] References Cited

U.S. PATENT DOCUMENTS

| | | | |
|---|---|---|---|
| 4,867,973 | 9/1989 | Goerd et al. | 424/85.91 |
| 4,925,648 | 5/1990 | Hansen et al. | 424/1.1 |
| 5,024,940 | 6/1991 | Brenner et al. | 435/69.1 |

FOREIGN PATENT DOCUMENTS

| | | |
|---|---|---|
| 3242389 | 5/1989 | Australia . |
| 6623590 | 5/1991 | Australia . |
| 0331034 | 2/1989 | European Pat. Off. . |
| 0336379 | 4/1989 | European Pat. Off. . |
| 0340109 | 4/1989 | European Pat. Off. . |
| 0417927 | 8/1990 | European Pat. Off. . |
| WO8912458 | 6/1989 | WIPO . |
| WO8912458 | 12/1989 | WIPO . |
| WO9006758 | 12/1989 | WIPO . |
| WO9006758 | 6/1990 | WIPO . |
| WO9013281 | 11/1990 | WIPO . |
| WO9013316 | 11/1990 | WIPO . |
| WO9103493 | 3/1991 | WIPO . |
| WO9206193 | 4/1992 | WIPO . |
| WO9207878 | 5/1992 | WIPO . |
| WO9213562 | 8/1992 | WIPO . |

OTHER PUBLICATIONS

Roitt Immunology Gower Medical Publishing 1985 p. 8.7 Fig. 8.19.
Williams et al J. Immunology 135(4):2249–2255 1985.
Geppert et al J. Immunology 138(6):1660–1666 1987.
Verwilghen et al Immunology 72:269–276 1991.
Harris et al Tibtech 11:42–46 1993.
Waldmann Science 252:1657–1662 1991.
Makinen et al JBL 264:3325–3334 1989.
Immunology, Roitt 1985 Grower Medical Publishing 15.g 20–2.
Springer Nature 342: 425–434 1990.
Martodam et al PNAS 76: 2128–2132 1979.
Makinen, et al JBL 264: 3325–3334 1989.
Ellenhorn, Transplantation 50: 608–12 (1990).
Hirsch et al., J. Immunol. 142:737–43 (1989).
Hirsch et al., The Lancet 1390 (1989).
Richards et al. New Eng. J. Med. 323:427–28 (1990).
Furukawa, K. et al. J. Immunol. Methods 131:105–112 (1990).
Huang et al., J. Biol. Chem. 258:14034–40 (1983).
Pastan et al., Science 254:1173–77 (1991).
Ellenhorn et al., Science 242:569 (1988).
Rodwell et al., Proc. Nat'l Acad. Sci USA 83:2632–36 (1986).
Baniyash et al., J. Immunol. 263: 9874 (1988).
Geisler et al., J. Immunol. 145: 1761 (1990).
Naversina et al., Abstract From Mechanism of Tumor Rejection II #7793 (1991).
Leo et al., Proc. Nat'l Acad. Sci. USA 84: 1374–78 (1987).
Beavchamp et al., Anal. Biochem. 131: 25 (1983).
Osband et al., Lancet 335: 994 (1990).
Williams et al., J. Immunol. 135: 2249 (1985).
Cueppens et al., J. Immunol. 137: 1816 (1986).
Geppert et al., J. Immunol. 138: 1660 (1987).
Kast et al., J. Immunol. 145: 2254 (1990).
Ellenhorn et al., J. Immunol. 144: 2840–46 (1990).
Hirsch et al., Transplantation 47: 853–57 (1989).
Hirsch et al., Transplantation 49: 1117–23 (1990).
Geppert, T.D. et al., J. Immunol. 138: 1660–66 (1987).
Harlow et al. *Antibodies: a laboratory manual*, Cold Spring Harbor Press 1986.
Martin J.I. 136 3282 1986.

*Primary Examiner*—Keith D. MacMillan
*Assistant Examiner*—J. D. Wessendorf
*Attorney, Agent, or Firm*—Eric P. Mirabel

[57] ABSTRACT

Several forms of immunoregulatory substances are derived from monoclonal antibodies (MAbs) that are specific for a T cell surface antigen, such as CD3, TCR, CD4, or CD8 on T cells. The substances include: a mixture of F(ab')$_2$ fragments (or other divalent binding molecules which lack Fc) which each bind noncompetitively to different monovalent antigenic epitopes on the same antigen; a conjugate including a polymer molecule, such as dextran, ficoll, or agarose, that is coupled with the binding molecules, e.g., Fv, Fab, or F(ab')$_2$, which bind to monovalent antigenic epitopes on the same antigen on T cells; a conjugate including a liposome or microbead that is coupled with the same binding molecules specific for a T cell surface antigen.

5 Claims, 4 Drawing Sheets

CONJUGATES OF MICROBEADS AND ANTIBODIES SPECIFIC FOR T LYMPHOCYTES AND THEIR USE AS IN VIVO IMMUNE MODULATORS

RELATED APPLICATIONS

This is a continuation of application Ser. No 07,819,449 filed on Jan. 10, 1992 now abandoned. This application is a continuation-in-part of U.S. application Ser. No. 07/688,000, filed Apr. 19, 1991, and priority to that application is hereby claimed.

FIELD OF INVENTION

The invention relates to immunoconjugates for modulating the immune system by inducing specifically the polyclonal activation, proliferation, and/or lymphokine production of T lymphocytes, or subsets thereof.

BACKGROUND OF THE INVENTION

Most immune responses involve many components of the immune system. Although the immune mechanisms involved in the elimination of malignantly transformed cells are not well understood, it is reasonable to assume that if more immune mechanisms are activated and enhanced, the tumorous cells may be eliminated more effectively. Also, both humoral and cellular mechanisms are known to be involved in the immune response against viruses and virus-infected cells. Thus, generally speaking, for the therapeutic treatments of patients with various cancers or infectious diseases, and for protecting individuals exposed to infectious agents from contracting the infection, it is desirable to enhance the entire immune system.

The various branches of the immune system include antibodies, cytotoxic T cells (CTLs), T cells mediating delayed-type hypersensitivities ($T_{TDH}$ cells), monocytes and macrophages, natural killer (NK) cells, K cells mediating ADCC, and granulocytes. regulatory roles, and many factors are secreted by these cells and other cells in a certain concerted fashion during the activation and proliferation phases. There is good reason to believe that the concerted production of lymphokines and cytokines, at the appropriate time and in the proper relative proportions, is important for maximizing the immune response.

Potentiation of the immune system is desirable for treating a number of pathologic conditions, e.g., for treatment of malignant tumors. The immune potentiators include substances identified from screening natural sources, such as cultures of microorganisms, marine animals, herbs, or plants, as well as substances screened from large batteries of synthetic organic compounds.

One example of a substance from a natural source is muramyl dipeptide, which has been identified as the smallest structure from the cell wall of staphylococcal bacteria which still retains immune potentiating effects. Many analogues of muramyl dipeptide have been synthesized. Muramyl dipeptide and its analogues are macrophage activators, and have been tested and developed as therapeutic agents for tumors and as adjuvants for vaccines.

Other examples of immune potentiators derived from natural sources include double-stranded RNA and mismatched double-stranded RNA (also called ampligen) which can induce interferon synthesis and other immune functions. These substances have also been tested for treating tumors and viral diseases, such as AIDS.

Immune potentiators may be applied to patients alone or in combination with surgery, irradiation, or chemotherapy. They may also be desirable for treating patients with viral infectious diseases or for protecting individuals, after exposure to viruses, from contracting infection. Immune potentiators may be useful as adjuvants for various vaccines for infectious diseases or cancers.

Recently, recombinant human lymphokines and cytokines have been produced by genetic engineering. Many such recombinant "biological response modifiers" are being tested for treatment of various cancers and infectious diseases. A few recombinant products, such as interleukin-2 (IL-2), α-interferon, γ-interferon, granulocyte-colony stimulation factor and granulocyte/monocyte-colony stimulation factor (G-CSF, GM-CSF), have been approved in many countries for use against certain cancers and infectious diseases. For example, IL-2 is approved for treating patients with renal cell carcinoma; α-interferon is approved for treating patients with hairy cell carcinoma or with hepatitis B infection; G-CSF and GM-CSF are approved for treating cancer patients receiving chemotherapy for the purposes of restoring lost neutrophils.

Individual recombinant lymphokines, such as IL-2, IL-4, or γ-interferon can augment some aspects of the immune system, but function only against limited immunocyte targets and can only potentiate certain immune functions and not the entire immune system. They also probably function only over short ranges and in limited areas in vivo. Also, cytokines and lymphokines which are injected into patients are cleared rapidly through the kidneys. They likely will not be present in sufficiently high concentrations in the lymphoid system for long enough to achieve their desired immunological effects.

Of the various substances other than lymphokines or cytokines which have been studied for potentiating the immune system, most which are suitable for in vivo use do not target or enhance the T cells directly. For example, muramyl dipeptide, and analogues thereof, primarily activate macrophages. Double-stranded RNA and mismatched double-stranded RNA mainly induce interferon production by a variety of cells.

A few naturally-derived protein substances are known to be potent T cell mitogens in culture in vitro, and have been used in studies to characterize and quantitate T cell activity. These substances include phytohemagglutinin A (PHA), concanavalin A (Con A), wheat germ agglutinin (WGA), and some other lectins, defined as carbohydrate-binding plant proteins. However, these T-cell mitogenic proteins, although very useful for in vitro studies, have poor specificity and therefore bind to almost all cell types. Because they are toxic and lack specificity, they are not effective for in vivo use as T cell potentiators.

In order to activate and expand lymphocytes to achieve satisfactory therapeutic effects while avoiding administering toxic substances, some groups have sought to activate and expand the T lymphocytes from patients in culture in vitro for a period of time under optimal conditions and then harvest the activated cells and inject them back into the same patients. In this so-called IL-2/LAK therapeutic regimen, used by the Biological Therapy Institute (Franklin, Tenn.) to treat patients with various cancers, the blood is first drawn from the patients and the mononuclear cells are isolated. See Rosenberg, S. A. et al., *N. Eng. J. Med.* 316:889 (1987). The cells are incubated in medium containing recombinant IL-2 for several weeks, and the activated and expanded T cells, which contain the lymphokine-activated killer (LAK) cells, are harvested and injected into the patients.

A more recent, modified version of this IL-2/LAK therapy, known as autolymphocyte therapy (ALT) has been developed by Cellcor Therapies, Inc. in Boston Mass. See Osband, M. E. et al., Lancet 335:994 (1990). The lymphocytes from renal cell carcinoma patients are taken twice. The first time, the lymphocytes are stimulated with antibodies specific for human CD3 antigen (anti-CD3) in vitro to produce lymphokines. The culture supernatant is collected after a few days of culturing, and the cells are discarded. The second time, the lymphocytes taken from the patients are incubated in the "autologous" lymphokines for a period of five days and the cells are harvested and injected into the same patients.

It is claimed that these approaches, involving in vitro lymphocyte stimulation and expansion, achieve beneficial responses in a portion of the treated patients. The major concern with these regimens is that the treatment is very tedious, expensive, and requires sophisticated, specialized cell culture facility. The variation among cells or cultures from different patients requires demanding monitoring procedures. Also, lymphocyte cultures have very poor viability even under optimal conditions, meaning that during the culturing, large numbers of the cells will die. When large numbers of dead cells are injected into patients, this may actually burden the reticuloendothelial system (RES) and reduce its effectiveness in combating the tumor cells.

In summary, the clinical studies and approved routine uses of IL-2 and γ-interferon and of LAK or ALT therapies indicate that T cell activation and expansion can achieve therapeutic effects in some patients with cancers or infectious diseases. On the other hand, the results of these treatments suggest that the lymphokine treatments have certain deficiencies and the LAK and ALT treatments have some substantial drawbacks. Thus, an efficacious and feasible treatment may be realized if these deficiencies can be eliminated.

A number of MAbs specific for CD3 on the surface of human T cells (pan T marker) are known to be very potent mitogens of human T cells in vitro, e.g., the MAb OKT3. Van Wauwe, J. P. et al., *J. Immunology* 124:2708 (1980); Chang, T. W. et al., *Proc. Natl. Acad. Sci. U.S.A.* 78:1805 (1981); MAb 64.1 Hansen, J. A. et al., *Leukocyte Typing: Human Leukocyte Differentiation Antigens Detected by Monoclonal Antibodies,* Eds. Bernard, A. et al. (Spring Verlag, New York, 1984). In medium containing only fetal calf serum and no human serum (and therefore no IgG), the anti-CD3 MAbs are much more potent than PHA or Con A in inducing T cell proliferation.

But the mitogenic effect of anti-CD3 requires both specific binding to the CD3 antigen and the presence of the Fc moiety of the antibody, as well as the presence of monocytes and macrophages. The best explanation for these results is that the Fc of the anti-CD3 MAbs binds to the Fc receptors on monocytes/macrophages, thereby aggregating the CD3 antigen on the T cell surface. Since CD3 is associated with the T cell antigen receptors, the aggregation of CD3 triggers the activation and proliferation of the T cells.

This explanation is supported by experiments which show that when the anti-human CD3 MAb is conjugated to Sepharose 4B beads or coated on the substratum plastic surface of culture wells, monocytes and macrophages are not needed to induce activation and proliferation of T cells. See Williams, J. M. et al., *J. Immunol.* 135:2249 (1985); Ceuppens, J. L. & Baroja, M. L., *J. Immunol.* 137:1816 (1986); Geppert, T. D. & Lipsky P. E., *J. Immunol.* 138:1660 (1987). Based on these experiments, it has been suggested that the solid-phase anti-CD3 MAb functions by aggregating the CD3 antigen on the T cell surface.

However, when anti-human CD3 is injected in vivo, the results are the opposite of the in vitro effects. OKT3 MAb, which is the first MAb ever approved for therapeutic use in vivo, is strongly immunosuppressive and is approved for use as an immunosuppressor for patients receiving kidney transplants. Ortho Multicenter Group Study, *N. Eng. J. Med.* 313:337 (1985). The injection of OKT3 causes rapid depletion of T cells from the circulation. Although the mechanism by which anti-CD3 causes this rapid depletion of T cells is not well understood, the best explanation is that anti-CD3 induces ADCC of the T cells, i.e., as the T cells coated by anti-CD3 circulate through the spleen and liver, they are lysed by the phagocytic cells of the RES in these organs. It is also possible that some of the T cells are destroyed by complement-mediated cytolysis and some other cytolytic mechanisms.

In in vivo mouse studies using a hamster MAb against murine CD3, it has been shown that low doses of anti-CD3 can prevent malignant progressive tumor growth and protect against lethal sendei virus infection. Ellenhorn, J. D. et al., *Science* 242:569 (1988); Kast, W. M. et al., *J. Immunol.* 145:2254 (1990). It has been suggested that the T cells in the mice are activated by such treatment with anti-CD3. Hirsch, R. et al., *J. Immunol.* 142:737 (1989).

Human and murine studies involving in vivo administration of anti-CD3 indicate that there is a substantial difference between the two species. In humans, even minute amounts of anti-CD3 administered intravenously are immunosuppressive and cytolytic. Also, the activation and mitogenic effect of anti-CD3 on T cells in vitro is completely blocked by the presence of human serum or IgG. Chang, T. W. et al., *Proc. Natl. Acad. Sci. U.S.A.* 78:1805 (1981); Looney, R. F. and Abraham, G. N. *J. Immunol.* 133:154 (1984). These results suggest that whole anti-CD3, or fragments thereof, will not activate T cells in humans in vivo, and therefore, the invention described below is not suggested.

SUMMARY OF THE INVENTION

The immunoregulatory substances of the invention include: a mixture of $F(ab')_2$ fragments (or other divalent binding molecules which lack Fc) which bind noncompetitively to different monovalent antigenic epitopes on the same antigen; the $F(ab')_2$ fragment (or other divalent binding molecules which lack Fc) of a bispecific antibody which has each of its binding sites derived from one of the two MAbs that bind noncompetitively (i.e., without significant hindrance from each other) to monovalent antigenic epitopes on the same antigen; a conjugate including a polymeric backbone, such as polyethylene glycol ("PEG"), cellulose, dextran, ficoll, agarose, an amino acid copolymer, a liposome, or a microbead that is coupled with an antibody-derived binding molecule that lacks Fc, e.g., Fv, Fab, or $F(ab')_2$, which bind to monovalent antigenic epitopes on the same antigen; a conjugate including a polymeric backbone, a liposome, or a microbead that is coupled with binding molecules, e.g., Fv, Fab, or $F(ab')_2$, wherein one of the binding molecules specifically targets the CD3 antigen on T cells and wherein the other binding molecule(s) specifically target one or more of the other antigen(s) on T cells, such as CD2, CD4, CD5, and CD8.

The immunoregulatory substances of the invention are specific for a surface antigen of T cells or subsets thereof. These antigens include: CD3, idiotype bearing receptor chains and other T cell receptor (TCR)-linked components; CD2, CD4, CD5, CD8, and other T cell-specific surface components. Many of these antigens contain only a single binding site for each MAb (i.e., a monovalent antigenic epitope).

The main use for the immunoregulatory substances is as immune potentiators, which activate and expand T cells or a subset of the T cells, and stimulate them to produce IL-2, γ-interferon, IL-1, IL-4, IL-6, tumor necrosis factor (TNF), or other lymphokines. Because T cells play central roles in the regulation of many branches of the immune system, the concerted secretion of a number of lymphokines will activate many immune mechanisms, whereas the administration of individual lymphokines will have a more limited effect.

Such immune potentiators may be used to treat patients with cancers or infectious diseases, or to protect individuals exposed to infectious agents from contracting the infections. Immune potentiators may be applied as adjuvants for vaccines.

Many of the antigens on T cells (or subsets thereof) contain only one antigenic epitope which is specific for one unique MAb. The one MAb fragment by itself cannot cross-link and aggregate the surface antigen, which is often required for cell activation. In contrast, the products of this invention are designed to cross-link and aggregate the surface antigens without triggering complement-mediated cytolysis or antibody-mediated cellular cytotoxicity (ADCC) in vivo.

In one embodiment, the invention includes F(ab')$_2$ fragments (and other divalent binding molecules lacking Fc) which accomplish these objectives. The first fragments of the invention (including F(ab')$_2$ and other divalent binding molecules) bind noncompetitively to monovalent antigenic epitopes on the same antigen. The second fragments of the invention (including F(ab')$_2$ and other fragments) are derived from a bispecific antibody which has each of its binding sites derived from one of the two MAbs that bind noncompetitively to monovalent antigenic epitopes on the same antigen.

In another embodiment, the invention includes a molecular backbone or base to which binding molecules (including Fv, Fab, and F(ab')$_2$) may be conjugated. The backbone may be PEG, cellulose, dextran, ficoll, agarose or other hydrophilic polymers. Active groups for cross-linking may be introduced by established methods. Alternatively, long chain peptides containing Lys or Cys residues may be synthesized. A preferred family of amino acid copolymers are synthesized by a routine method, containing Gly, Ser, and Lys (or Cys) at 20:4:1 ratio, with molecular weights of 10,000 to 1,000,000 (about 150 to 15,000 amino acid residues long). Liposomes or microbeads formed by cross-linked polymers such as dextran or agarose, may also be used as the base for conjugating antibody fragments. These liposomes and microbeads are preferably about 1 to 10 μm in diameter and can be suspended homogenously in a liquid medium by agitation.

DETAILED DESCRIPTION OF MAKING AND USING THE INVENTION

Figure 2:
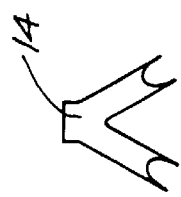
FIG. 2 A schematic illustration of a F(ab')$_2$ fragment of a MAb, which two Fab arms are identical and which is specific for one of the monovalent antigenic epitopes of the surface molecule in FIG. 1.

As noted above, the immunoregulatory substances of the invention include: a mixture of F(ab')$_2$ fragments (or other divalent binding molecules which lack Fc) which each bind noncompetitively to different monovalent antigenic epitopes on the same antigen; the F(ab')$_2$ fragment (or other fragments which lack Fc) of a bispecific antibody which has each of its binding sites derived from one of the two MAbs that bind noncompetitively to monovalent antigenic epitopes on the same antigen; a conjugate including a polymeric backbone, such as PEG, cellulose, dextran, ficoll, agarose, or an amino acid copolymer, or a liposome, or a microbead that is coupled with an antibody-derived binding molecule that lacks Fc, e.g., Fv, Fab, or F(ab')$_2$, which bind to monovalent antigenic epitopes on the same antigen; a conjugate including a polymeric backbone, a liposome, or a microbead, that is coupled with two or more antibody-derived binding molecules that lack the Fc portion, e.g., Fv, Fab, or F(ab')$_2$, wherein one of the binding molecules specifically targets the CD3 antigen on T cells and wherein the other binding molecule(s) specifically target one or more of the other antigen(s) on T cells, such as CD2, CD4, CD5, and CD8.

The Fv fragments of the MAbs may be produced in bacteria using single chain antibody technology, as described in U.S. Pat. No. 4,946,778 and International Application No. W088/09344. The Fv may also be genetically engineered to contain glycosylation sites and produced in mammalian cells, to result in a fragment containing carbohydrate moieties.

The Fab or F(ab')$_2$ may be produced by enzymatic cleavage of whole IgG which is produced by a hybridoma or a transfected cell lines (a myeloma or a cell line such as CHO), using pepsin and papain digestion, respectively.

The Fab or F(ab')$_2$ fragments may be wholly animal or human derived, or they may be in chimeric form, such that the constant domains are derived from the constant regions of human immunoglobulins and the variable regions are derived from the parent murine MAb. Alternatively, the Fv, Fab, or F(ab')$_2$ may be humanized, so that only the complementarity determining regions (CDR) are derived from an animal MAb, and the constant domains and the framework regions of the variable regions are almost entirely of human origin. These chimeric and humanized fragments are less immunogenic than their wholly animal counterparts, and thus more suitable for in vivo use, especially over prolonged periods.

Methods of making chimeric and humanized antibodies are well known in the art, (see, e.g., U.S. Pat. No. 4,816,567, International Application No. W084/03712, respectively). The Fv, Fab, or F(ab')$_2$ fragments may be produced from such chimeric or humanized antibodies using proteolytic digestion, as described above.

The antibody fragments can be conjugated to the linear or cross-linked backbone of a liposome using conventional techniques. See, e.g., Ostro, M. J. (Ed.), *Liposomes: from Biophysics to Therapeutics* (Marcel Dekker, New York, 1987). One preferred method of preparing liposomes and conjugating immunoglobulins to their surface is described by Ishimoto, Y. et al., *J. Immunol. Met.* 75:351 (1984). Multilamillar liposomes composed of dipalmitoylphosphatidylcholine, cholesterol and phosphotidylethanolamine are prepared. Purified fragments can then be coupled to the phosphatidylethanolamine by the cross-linking agent N-hydroxysuccinimidyl 3-(2-pyridyldithio) propionate. The coupling of the fragment to the liposome can be demonstrated by the release of a pre-trapped marker, e.g., carboxyfluorescence, from the liposomes upon the treatment of secondary antibody against the conjugated fragment and complement. Liposomes have different sizes, ranging from 0.1 to 5 $\mu$m in diameter.

The antibody fragments may also be coupled to microbeads. These microbeads are preferably about 1 to 10 $\mu$m in diameter (i.e., equal to or smaller than the diameter of resting blood lymphocytes), which allows them to be suspended in a liquid medium suitable for pharmaceutic administration in vivo. When agitated, the microbead suspension remains homogenous for at least several minutes, allowing time for withdrawal of the suspension and administration of it to a patient. The Sepharose 4B beads used for immobilizing anti-CD3 antibodies for in vitro studies of T cell activation (Williams, J. M. et. al., *J. Immunol.* 135:2249 (1985)) are about 45–165 $\mu$m in diameter. These large Sepharose 4B beads settle readily, and do not remain suspended for a sufficient period to allow withdrawal and administration of a homogenous suspension. Also, the beads are so large that they can not pass through the bore of needles of smaller diameters (or higher guage numbers). For in vivo administration, the preferred microbeads should be stable for relatively long periods, and yet be subject to degradation by the hydrolases in body fluids. Such microbeads include those made by cross-linking, in a well-established manner, agarose or dextran, one example of which is Superose 12 (Pharmacia LKB Biotechnology, Piscataway, N.J. 08854).

The antibody fragments may be coupled to the liposome, the microbead, or another carrier of the invention, via their carbohydrate moieties. Provided that the carbohydrate moiety is not in the hypervariable region or at the antibody binding sites, the conjugation via the cross-linking with the carbohydrate will not affect binding, as the binding sites will still be available to bind to cell surface antigens.

One preferred way to couple fragments of the invention (other than Fv) to a polymer backbone, a liposome, or a microbead is to conjugate them through the carbohydrate moiety on the constant regions. This will maximize the binding sites which are available and not hindered for binding to the antigens.

Methods for derivatizing sugar ring moities to create hydrazide groups for coupling with fragments (and antibodies) have been established. See Rodwell, J. D. et al., *Proc. Natl. Acad. Sci. U.S.A.* 83:2632 (1986). Several immunoconjugates prepared in this way are in clinical studies or pending approval for routine clinical uses.

The polymers for conjugating to the antigen binding sites can be modified to generate active groups for coupling according to established methods. For example, PEG can be derivatized by 1,1'-carbonyldiamidazole to form imidazole carbamate active groups, which react with amino groups of proteins. Beauchamp, C. O. et al., *Anal. Biochem.* 131:25 (1983). Similar reactions can be used for derivatizing agarose. Bethell, G. S. et al., *J. Biol. Chem.* 254:2572 (1979).

The antibody fragments can be coupled directly to the derivatized, activated polymers. Bifunctional cross-linkers suitable for conjugating the activated polymers (or liposomes or microbeads) and the fragments, can be selected based on the properties desired and the specific substances to be cross-linked. These heterobifunctional reagents are available from several commercial sources, e.g., Pierce Chemical Co., Rockford, Ill., and the reaction procedures are well-known.

The substances of the invention, in appropriate pharmaceutical vehicles, may be administered intravenously (i.v.), so that they can reach the T cells in circulation, spleen, liver, and various lymph nodes.

The substances of the invention may also be given intraperitoneally (i.p.), where they will mainly interact with cells in the peritoneal cavity and will be delivered to other lymphoid tissues through the lymphoid circulation. The T cells which are activated and expanded in the spleen and peritoneal cavity may also migrate to different tissues.

The substances of the invention may also be injected directly into or near the solid tumors, warts, or other affected tissues. In this case, the local T cells will be activated and expanded and mediate various immune mechanisms efficiently.

Certain substances of the invention may only induce the activation of resting lymphocytes and not their proliferation. In such case, their administration may be followed by T cell growth factors, such as IL-1, IL-2, or IL-4.

The substances of the invention may be given alone, or in combination with surgery, irradiation treatment, or chemotherapy for cancer patients, or in combination with viral antibiotics or other anti-viral substances for patients with infectious diseases. Certain of the substances of the invention may be given as adjuvants for vaccines or infectious diseases.

There is adequate experimental support for the immunopotentialing applications of the unique substances of the invention. As noted above, the interaction between the Fc of the anti-CD3 MAbs and the Fc receptors (FcR) on monocytes/macrophages is required both for the mitogenic effect in vitro and the ADCC effect in vivo. It was first found that the F(ab')$_2$ and Fab fragments of OKT3, which lacked Fc, were no longer mitogenic and also that whole OKT3 could not induce the T cells to proliferate if the monocytes were depleted from the mononuclear cells in culture. Van Wauwe, J. P., et al., *J. Immunol.* 124:2708 (1980); Chang, T. W., et al., *Proc. Natl. Acad. Sci. U.S.A.* 78:1805 (1981). It was then suggested that the mechanism of anti-CD3 mitogenic effect involved the interaction between the Fc of anti-CD3 and FcR on monocytes, because human serum, purified human IgG, or isolated Fc fragments could block the mitogenic effect of OKT3. Looney, R. F. and Abraham, G. N., *J. Immunol* 133:154 (1984); Chang, T. W., *Immunol. Today* (1985). Several studies also showed that the deficiency of FcR for IgG on monocytes would impair the mitogenic effects of anti-CD3, supporting the notion that Fc-FcR interaction is important for the mitogenic effects of anti-CD3. Ceuppens, J. L., et al., *J. Immunol.* 135:3882 (1982); Tax, W. J. M., et al., *Nature* 304:445 (1983); Tax, W. J. M., *J. Immunol.* 133:1185 (1984).

A few studies examined the mitogenic mechanism of anti-CD3 further. It was found that anti-human CD3 MAb densely conjugated to Sepharose 4B beads and purified human IL-1 could induce the proliferation of T cells in culture in which the antigen presenting monocytes were completely depleted. It was concluded that the anti-human CD3 MAb-Sepharose 4B could activate the resting human T cells and the IL-1 was then able to initiate the synthesis of RNA, IL-2 secretion, IL-2 receptor expression, and ultimately, DNA synthesis. Williams, J. M., et al., *J. Immunol.* 135:2249 (1985). It was also reported that in the complete absence of monocytes, the T cells could be induced to proliferate by incubation in plastic culture plates coated with anti-human CD3 MAb, if soluble anti-human CD5 MAb was also provided in the culture medium. Ceuppens, J. L. and Baroja, M. L., J. Immunol. 137:1816 (1986). Later it was reported that the resting T cells depleted of accessory monocytes could proliferate in wells of microtiter plates coated with high concentration of anti-human CD3 (for 64.1 MAb, 40–1000 ng/ml) without the addition of IL-2 or monocytes. Geppert, T. D. and Lipsky, P. K., *J. Immunol.* 138:1660 (1987).

These results show that the "solid-phase" anti-human CD3 can stimulate T cell activation and/or proliferation in the absence of monocytes. However, solid plastic sheets or Sepharose 4B beads which are coated with intact IgG of anti-CD3 MAbs, although suitable for in vitro use, are not appropriate for in vivo use. The coated antibodies can absorb both T cells and macrophages. In addition, these solid materials, whether deposited i.p. or by other routes, will be maintained in situ. For in vivo use, hydrophilic, soluble polymers, liposomes, or microbeads suitable for conjugating large numbers of anti-human CD3 MAb molecules are preferred.

When anti-CD3 MAb molecules are conjugated to the polymer backbones, liposomes, or microbeads, the Fc portion of anti-CD3 MAb will be accessible to monocytes and macrophages and other cells of the RES, and hence will facilitate phagocytosis and clearance of such conjugates. To minimize such clearance and to ensure that the mitogenic effect of anti-CD3 will be the dominant effect, and that any suppressive effect mediated by ADCC and complement-mediated cytolysis will be the lessened to low levels, fragments of anti-CD3 MAbs which are devoid of the Fc domains (i.e. Fv, Fab, and F(ab')$_2$) and which do not cause the Fc-dependent ADCC and complement-mediated cytolysis, are conjugated to the polymer backbones, liposomes, or microbeads. The experiments with solid-phase bound anti-CD3 MAbs suggest that under certain conditions, the Fc domain of the antibody is not required in mitogenesis.

Among the surface molecules that are involved in the regulation of the activities of lymphocytes, the most important are the components or molecules associated with the TCR on T cells. These antigen receptors interact with antigens or antigen-presenting cells, and respond to antigen stimulation by causing the cell to undergo a sequence of activation, clonal expansion, and differentiation. The activation and expansion of lymphocytes consequently leads to various immune reactions and responses.

The TCR complex is very complicated and the structure is not fully characterized, despite extensive study. The information available indicates that the "complete" TCR complex contains one $\alpha$ chain, one $\beta$ chain, one $\gamma$ chain, one $\epsilon$ chain, one $\delta$ chain, and a homodimer $\zeta$ chain. The $\alpha$ and $\beta$ chains are clonally different and $\alpha/\beta$ dimer is customarily referred to as the TCR. The remaining components of the TCR complex ($\gamma$, $\epsilon$, $\zeta$, and $\delta$ chains) are not polymorphic and are categorically referred to as the CD3 antigen.

It is known that T cells at different differentiation stages or with different functions express different sets of the chains. See e.g., Baniyash, M. et al., *J. Immunol.* 263:9874 (1988); Geisler, C. et al., *J. Immunol.* 145:1761 (1990). Thus, within the TCR complex on most T cells, the antigenic epitopes recognized by most MAbs are monovalent (one single epitope per complex).

It is possible that since there are two $\zeta$ chains in the TCR complexes of some T cells, there may be two antigenic sites for some MAbs recognizing CD3$\zeta$ chain. Among these MAbs, some may be able to cross-link the CD3/TCR complexes. Because the $\zeta$ chain is relatively small (16 Kd), only a small portion of it is exposed to the exterior surface. Some MAbs specific for the CD3-$\zeta$ dimer may bind to one of the two divalent antigenic epitopes which are physically close together and preclude the binding of another anti-CD3-$\zeta$ MAb at the same site. Thus, for practical purposes, this latter group of MAbs (which is likely a small group), although they also bind to divalent antigenic sites, they cannot cross-link the CD3/TCR complexes.

It has been suggested that in the mitogenesis of T cells with anti-CD3, the monocytes, through the interaction between Fc of anti-CD3 and the FcR on monocytes, can aggregate the CD3 antigen on the surface of T cells. Since CD3 is associated with the TCR, the aggregation of the TCR complexes triggers the activation and subsequent proliferation of the T cells. Some MAbs specific for the CD3-$\zeta$ chain may recognize a divalent antigenic epitope and can cross-link and aggregate the CD3/TCR complexes. Most anti-CD3 MABs are likely specific for a monovalent antigenic epitope on CD3-$\gamma$, CD3-$\epsilon$, or CD3-$\delta$, or even on CD3-$\zeta$. Thus anti-CD3 MAb in soluble form cannot trigger activation and proliferation of T cells because the antigenic epitopes on the CD3 molecules which are recognized by anti-CD3 MAb are likely monovalent. Accordingly, the MAb or F(ab')$_2$ can bridge the surface molecules and form multiple pairs of CD3, but cannot cross-link and aggregate them. Thus, by using two or more anti-CD3 MAbs, each binding to a monovalent antigenic epitope on CD3 in a noncompetitive fashion, the CD3 antigen may be cross-linked and aggregated, and thereby, the T cells will be triggered to activate and proliferate. To avoid the cytotoxicity caused by the Fc domain of the anti-CD3 MAb, F(ab')$_2$ derived from whole IgG, or genetically engineering F(ab')$_2$, are preferred.

Figure 1:
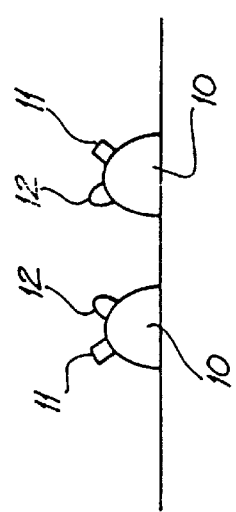
FIG. 1 A schematic representation of a surface molecule that has two monovalent antigenic epitopes, each recognized by a different MAb binding site.
Figure 3:
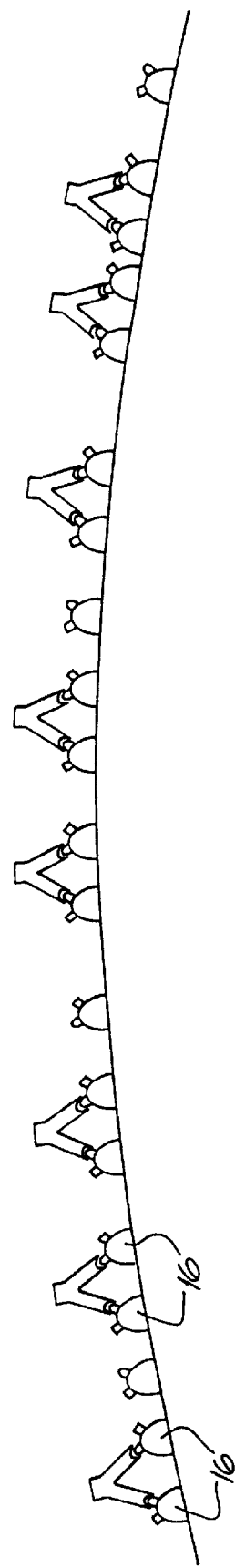
FIG. 3 A schematic representation showing the formation of pairs of molecules by the bridging of the F(ab')$_2$ of FIG. 2.

FIG. 1 schematically illustrates that a particular antigen molecule 10 contains two monovalent antigenic epitopes, 11 and 12 respectively, each recognized by one MAb fragment. FIG. 2 shows the F(ab')$_2$ of one of such MAb fragment 14. The MAb fragment 14 will cause the formation of paired antigens 16 on the surface of T cells, as shown in FIG. 3.

Figure 4:
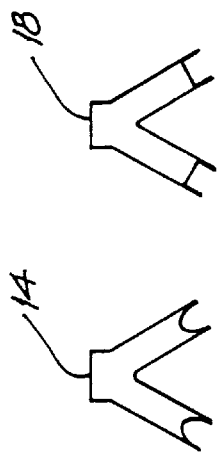
FIG. 4 A schematic representation of a mixture of two F(ab')$_2$ of two MAbs each specific for one of the monovalent antigenic epitopes of the surface molecule in FIG. 1.
Figure 5:
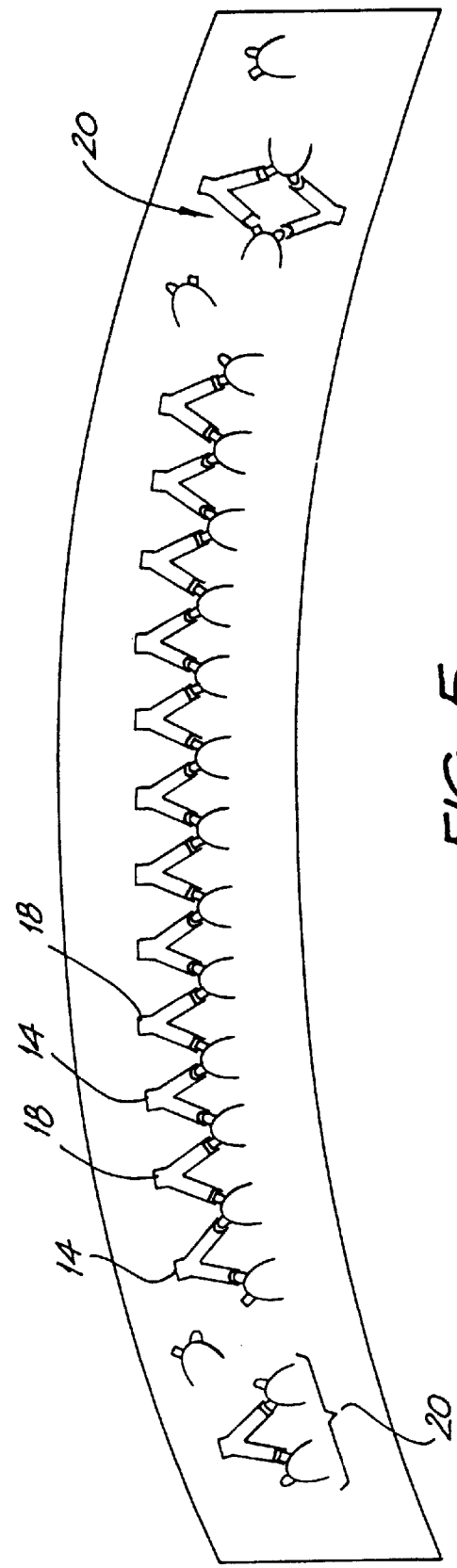
FIG. 5 A schematic representation showing the cross-linking of the surface molecules of FIG. 1 by the mixture of the two F(ab')$_2$ of FIG. 4. Note some singly-paired molecules are also formed.

To cause cross-linking and aggregation without the help of monocytes, two or more MAb fragments, each recognizing a monovalent antigenic epitope, are required. FIG. 4 schematically shows the mixture of two F(ab') (14 and 18), each recognizing one of the two antigenic epitopes 11 and 12. FIG. 5 shows that by using the F(ab')$_2$ 14 and 18, a degree of cross-linking and aggregation can be achieved, but that some pairs of molecules 20 will also be linked. It can be appreciated that if three different anti-antigen MAbs are used, the cross-linking and aggregation will be even more pronounced.

Figure 6:
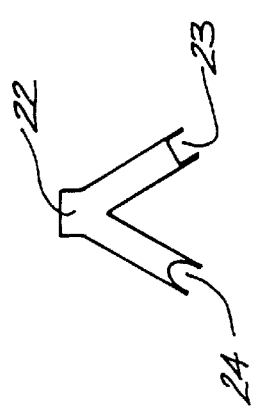
FIG. 6 A schematic representation showing a bispecific F(ab')$_2$ which is specific for both of the two different monovalent antigenic epitopes of the surface molecule of FIG. 1.
Figure 7:
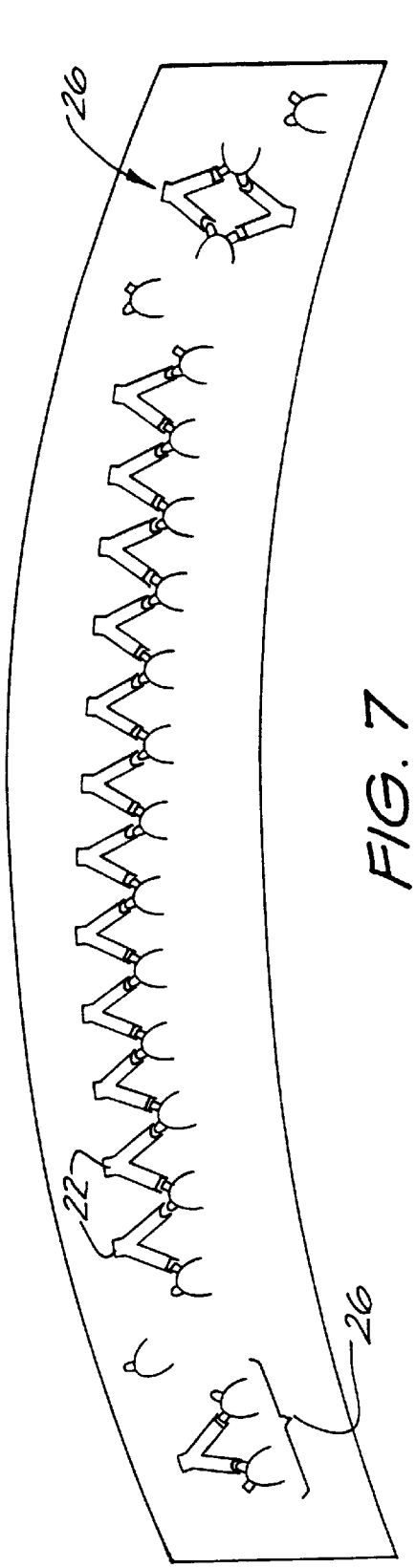
FIG. 7 A schematic representation illustrating the cross-linking of the surface epitopes of FIG. 1 by the bispecific F(ab')$_2$ of FIG. 6. Some paired molecules are formed.

FIG. 6 shows schematically a bispecific F(ab')$_2$ 22 with two specificities, 23 and 24, respectively being for the monovalent antigenic epitopes of CD3, 11 and 12. FIG. 7 shows that with this bispecific fragment 22, cross-linking and aggregation of molecules can be achieved, although some singly-paired molecules 26 are left on the T cell surface. These F(ab')$_2$ preparations will therefore also induce T cell activation and proliferation.

Another means to achieve cross-linking of antigenic epitopes on T or B cell surfaces is to use plastic sheets and Sepharose 4B beads coated or conjugated with anti-CD3 MAbs. These may be implanted or deposited into certain body sites in order to trigger mitogenesis. However, as noted above, such preparations cannot be transported through the lymphoid circulation, nor can they be administered i.v. Thus, the appropriate backbone or base upon which to conjugate anti-CD3 MAb should be polymers which are hydrophilic, stable, non-immunogenic, nontoxic and resistant to hydrolases (e.g. glycosidases and proteases) in the serum and other body fluids in patients. Examples are PEG, cellulose, dextran, ficoll, and agarose, which each have different molecular sizes and are all well-characterized and studied.

Another suitable "backbone" is an amino acid copolymer. One preferred amino acid copolymer includes Gly and Ser residues, and Lys, Cys, or another appropriate residue, for providing conjugation sites. Considering the molecular sizes of Fv, Fab, and F(ab')$_2$, the optimal spacing between the adjacent Lys or Cys residues is in the range of 15 to 25 amino acids. Thus, a preferred amino acid copolymer has a composition of $(Gly_{15}Ser_{15}Lys)_n$, where n is 5 to 600.

The fragments of the invention can also be conjugated to liposomes, using the methods described above, wherein reactive groups for cross-linking are introduced on the surface of the liposomes and the fragments are coupled thereto. For certain clinical applications with certain MAbs, fragments (or binding molecules) conjugated to liposomes may be more preferred than fragment/polymer conjugates, as the liposome conjugates can interact with antigen on T cells by a mechanism more closely resembling the interaction between cells, than when the fragment is presented on a polymer backbone.

The fragments of the invention can also be conjugated to microbeads. The chemical composition of the microbeads are similar to the Sepharose 4B or Sephadex beads, although the microbeads are preferably smaller in size (preferably about 1 to 10 μm in diameter) than the Sepharose 4B or Sephadex beads typically used in chromatography.

The Sepharose 2B, 4B, and 6B beads which have different degrees of cross-linking of agarose molecules, have wet bead diameters of about 60–200, 45–165, and 45–165 μm, respectively. The Sephadex beads, which also come in forms of different degrees of cross-linking of dextran molecules, have wet bead diameters of about 20–600 μm. Even the finest Sephadex beads (Sephadex G-25 SF) have wet bead diameters of 17.2–69 μm. These beads are much larger than white blood cells, which have diameters of about 10–15 μm. They are made for chromatography and readily settle after agitation. Many other kinds of beads which are produced by the cross-linking of agarose or dextran and are marketed by Pharmacia LKB Biotechnology, have minimum bead diameters of about 20 μm. However, Superose 12 HR 10/30 beads have diameters of 10±2 μm. The Superose 12 beads are about the size of small, resting lymphocytes. Since blood leukocytes can be readily suspended and administered to patients, Superose 12 beads conjugated with antibodies have similar physical properties, and can also be easily suspended and withdrawn into syringes for in vivo administration. Beads of smaller sizes may be made by the same chemistry. The beads of smaller sizes may be fractionated from those of larger sizes by their sedimentation rate in a liquid suspension.

The mitogenicity of the polymerized fragments of the invention probably depends on their sizes; more specifically, on the number of binding sites per molecular conjugate. The preferred molecular conjugates are those which are small but still are able to induce optimal mitogenic effects. Many suitable polymers are available commercially in different lengths or sizes. Amino acid copolymers of different lengths can also be synthesized and fractionated by molecular sieve chromatography. Polymers such as cellulose or agarose can be treated with specific enzymes, e.g., cellulase and agarase, to yield different lengths.

Figure 8:
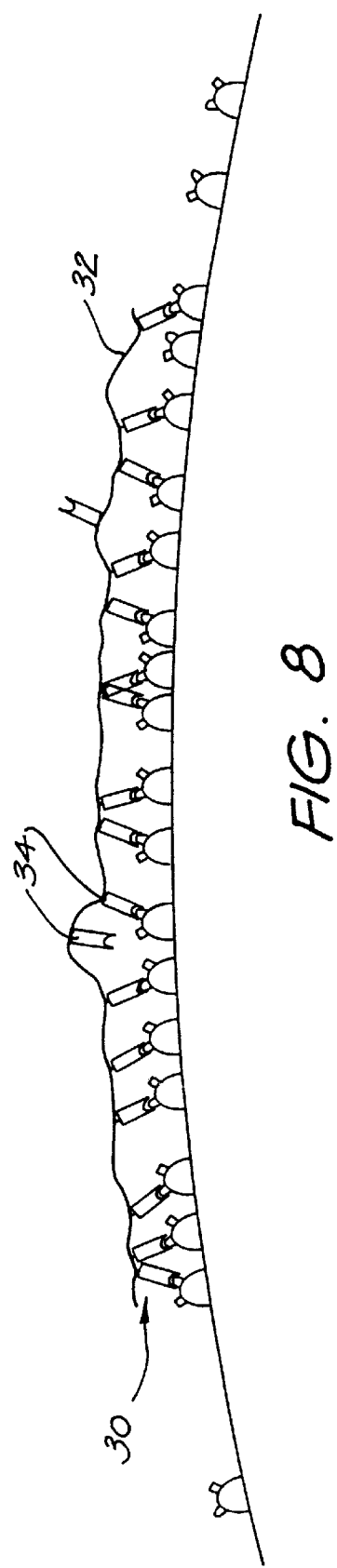
FIG. 8 A schematic representation showing the cross-linking of the surface epitopes by a monospecific polymerized MAb.

FIG. 8 schematically shows that cross-linking and aggregation of surface molecules can be achieved by using a molecular conjugate 30 consisting of a polymer backbone 32 coupled with the monovalent Fab fragment 34 specific for the monovalent antigenic epitope 12 of FIG. 1. The molecular conjugates may also be attached to liposomes or microbeads in order to achieve maximal activation of the T cell.

Figure 9:
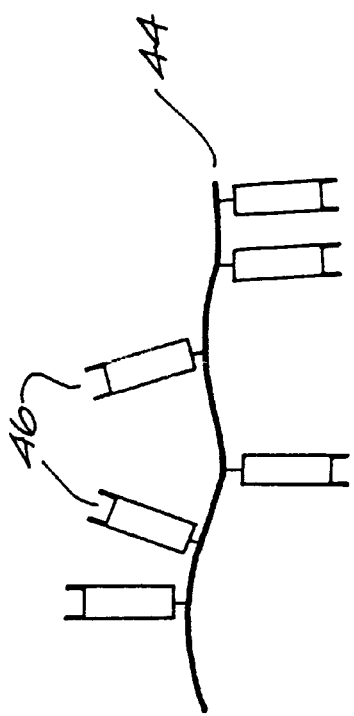
FIG. 9 A schematic representation showing the mixture of two molecular conjugates, each consisting of a polymeric backbone coupled with the Fab of a MAb specific for one of the two monovalent antigenic epitopes of the surface molecule of FIG. 1.
Figure 10:
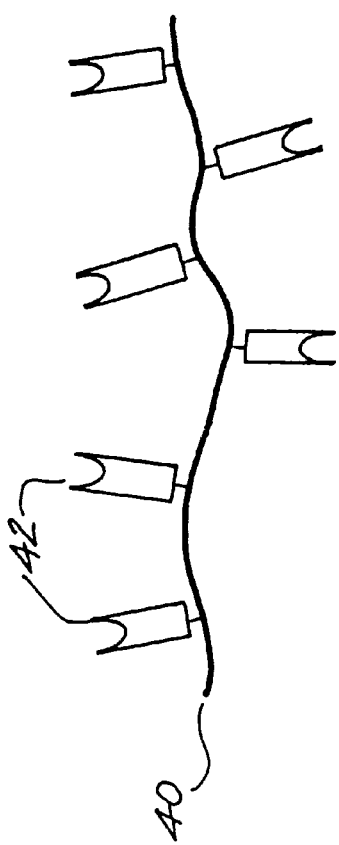
FIG. 10 A schematic representation showing the molecular conjugate of a polymeric backbone coupled with two Fab of two different MAbs, each specific for one of the two monovalent antigenic epitopes of the surface molecules of FIG. 1.

In keeping with the notion that smaller molecular conjugates or particles are preferred provided good cross-linking and aggregation can be obtained, some other embodiments, schematically shown in FIGS. 9 and 10, are also included. Referring to FIG. 9, a polymer backbone 40 (which can also be a microbead) is coupled with a monovalent Fab fragment 42 against antigenic epitope 12 of FIG. 1, and a polymer backbone 44 is coupled with a monovalent Fab fragment 46 against antigenic epitope 12 of FIG. 1. In FIG. 10, a polymer backbone 50 (which can also represent a microbead) is coupled with Fab fragments 41 and 46.

These embodiments function similarly in principle to the two products shown in FIGS. 4 and 6, the difference being that there are more binding sites in the molecular conjugates than in the F(ab')$_2$ of FIGS. 4 and 6. Because of the larger numbers of binding sites, the cross-linking and aggregation will be more complete and there will be fewer singly-paired molecules, which are not cross-linked. Because liposomes and microbeads have relatively ordered surfaces for presenting the antibody fragments to T cells, in another embodiment of the invention, the conjugates of antibody fragments and polymers, such as dextran-anti-CD3 Fab, are attached to liposomes and microbeads for T cell activation.

As noted above, the invention is not limited to anti-CD3 fragments, but also includes binding molecules, fragments (and conjugates thereof) which are specific for surface antigens of human T lymphocytes, and which have immunoregulatory activities in vivo, when administered according to the techniques of the invention. As is true for anti-CD3, many of these in vivo effects would not be predicted from the known in vitro effects or the in vivo effects with the whole antibodies. The desirable stimulatory effects of such products, that are prepared according to the present invention, will result even though the in vivo effects of IgG specific for T cells are primarily cytolytic effects mediated by complement, ADCC, or other cytolytic mechanisms. In addition to anti-CD3, other examples of antibodies which initiate these cytolytic effects in vivo are anti-CD4 antibodies, Alters, S. E., et al., *J. Immunol.* 144:4587 (1990). All of these antibodies cause T cell depletion in vivo.

Anti-CD4 and antibodies against B cell antigen receptors have been found to have stimulatory effects in vitro. This indicates that, like anti-CD3, when formulated according to the invention, they would activate or modulate their respective target cells in vivo. A number of studies have indicated that the activation of T cells with an anti-CD3 MAb can be enhanced by an MAb which is specific for a different surface antigen on T cells. These auxiliary MAbs include those specific for HLA class-I antigens, HLA class-II antigens (such as Ia), CD2, CD4, CD5, CD8, CD28, or CD37. Ceuppens, J. L. et al., *J. Immunol.* 137:1816 (1986); Tutt, A. et al., *J. Immunol.* 147:60 (1991). Some of these antigens, such as HLA and CD37, are expressed by many cell types. Thus, the MAbs which target these antigens, whether used alone or in combination with anti-CD3 MAbs, are not preferred due to their lack of specificity. Nevertheless, some of these antigens, such as CD2, CD4, CD5, and CD8, are specifically expressed by T cells or subsets of T cells. Thus, in one embodiment of the invention, a fragment of anti-CD3 MAb and a fragment of an anti-CD2, anti-CD4, anti-CD5, anti-CD8, or other MAb specific for T cells, is conjugated to a polymer backbone, a liposome, or a microbead. The polymerized or immobilized pairs of MAbs, both of which are devoid of Fc portions, can then be used to activate T cells in vivo.

It is noted that, unlike the fragments of the invention which are mixtures of fragments binding to at least two different antigenic determinants, single MAbs which bind to monovalent antigenic determinants cannot cross-link the antigens on the cell surface. In order to stimulate cell activation and proliferation, cross-linking of the surface antigens is usually required. However, many surface molecules such as CD4 are single polypeptide chains or are composed of different polypeptide chains, and cannot be efficiently cross-linked by a single divalent antibody recognizing monovalent antigenic epitopes.

EXAMPLES

Testing Anti-CD3 MAbs for Noncompetitive Binding to CD3 on T cells

Various anti-CD3 MAbs can be purchased from commercial firms offering immunochemical reagents, including Ortho Diagnostic Systems, Raritan, N.J.; Becton Dickenson Immunological Reagents, Mountain View, Calif.; Coulter Diagnostics, Hialeach, Fla.; Sigma Chemical Co., St. Louis, Mo.; Boehringer Mannheim, Indianapolis, In.; Olympus Corp., Lake Success, N.Y. All these MAbs were developed by different groups. These firms offer anti-CD3 MAb not only in purified, plain IgG, but also in fluorescein-conjugated forms.

Additional MAbs against human CD3 can be readily prepared by hybridoma methodology as described by Kung, P. C. et al., *Science* 206:347 (1979). Using this method, many laboratories have developed murine anti-human CD3 MAb.

For determining whether two MAbs (or fragments) specific for human CD3 can bind to CD3-bearing T cells simultaneously, fluorescence flow cytometric analyses may be applied. For these analyses a human T cell line, such as CEM (ATCC CCL119 from the American Type Culture Collection), or peripheral blood mononuclear cells, can be used for the cell staining. The assay is to determine whether the binding of a FITC or rhodamine-labeled anti-CD3 MAb to the cells will be inhibited by the presence of varying concentrations of a second anti-CD3 MAb. The assay should also be reversed to determine whether the binding of the fluorescence-labeled second anti-CD3 is inhibited by the presence of the other anti-CD3.

If the binding of each anti-CD3 to the T cells is not signficantly affected by 5–10 fold concentrations of the other anti-CD3, it can be concluded that both anti-CD3 MAb can bind non-competitively to CD3 molecules on T cells. Additional confirming assays would measure whether the binding to T cells by the two MAbs is additive.

It should be understood that the terms and expressions described herein are exemplary only and not limiting, and that the scope of the invention is defined only in the claims which follow, and includes all equivalents of the subject matter of those claims.

What is claimed is:

1. A composition comprising a microbead coupled with a plurality of binding molecules which lack Fc portions and which are specific for CD2, CD3 or other T cell receptor-linked components, CD4, CD5, or CD8.

2. A composition of claim 1, wherein the microbead is hydrophilic, stable, and nonimmunogenic in humans, and resistant to hydrolysis in human body fluids.

3. A composition of claim 1, wherein the microbead is about 1 to 10 $\mu$m in diameter.

4. A composition of claim 1, wherein the microbead is made by cross-linking agarose or dextran.

5. A composition of claim 1, wherein the binding molecule is selected from the group consisting of Fv, Fab, and F(ab')$_2$ of antibodies.

* * * * *